US009259736B2

(12) United States Patent
Corbett

(10) Patent No.: US 9,259,736 B2
(45) Date of Patent: Feb. 16, 2016

(54) THERMAL CYCLING DEVICE

(75) Inventor: John Corbett, Morelake (AU)

(73) Assignee: QIAGEN INSTRUMENTS AG, Hombrechtikon (CH)

( * ) Notice: Subject to any disclaimer, the term of this patent is extended or adjusted under 35 U.S.C. 154(b) by 326 days.

(21) Appl. No.: 12/743,788

(22) PCT Filed: Nov. 27, 2008

(86) PCT No.: PCT/AU2008/001752
§ 371 (c)(1),
(2), (4) Date: Aug. 31, 2010

(87) PCT Pub. No.: WO2009/067744
PCT Pub. Date: Jun. 4, 2009

(65) Prior Publication Data

US 2010/0323923 A1 Dec. 23, 2010

(30) Foreign Application Priority Data

Nov. 30, 2007 (AU) ................................ 2007906569

(51) Int. Cl.
*B01L 5/00* (2006.01)
*C40B 60/00* (2006.01)
*C12M 1/38* (2006.01)
*H05B 6/00* (2006.01)
*B01L 7/00* (2006.01)
*B01L 3/00* (2006.01)
*B01L 9/06* (2006.01)

(52) U.S. Cl.
CPC ........... *B01L 7/5255* (2013.01); *B01L 3/50851* (2013.01); *B01L 7/52* (2013.01); *B01L 9/06* (2013.01); *B01L 2200/147* (2013.01); *B01L 2300/0803* (2013.01); *B01L 2300/1844* (2013.01); *B01L 2300/1861* (2013.01); *B01L 2300/1872* (2013.01); *B01L 2300/1894* (2013.01)

(58) Field of Classification Search
None
See application file for complete search history.

(56) References Cited

U.S. PATENT DOCUMENTS 4,683,195 A 7/1987 Mullis et al.
4,683,202 A 7/1987 Mullis
4,800,159 A 1/1989 Mullis et al.
4,889,818 A 12/1989 Gelfand et al.
4,965,188 A 10/1990 Mullis et al.
4,988,617 A 1/1991 Landegren et al.
5,023,171 A 6/1991 Ho et al.
5,066,584 A 11/1991 Gyllensten et al.
(Continued)

FOREIGN PATENT DOCUMENTS

WO 92/20778 A1 11/1992
WO 98/49340 A1 11/1998
WO 01/03838 A1 1/2001

OTHER PUBLICATIONS

International Search Report, PCT/AU2008/001752, Feb. 3, 2009 (3 pages).

*Primary Examiner* — P. Kathryn Wright
(74) *Attorney, Agent, or Firm* — Miles & Stockbridge PC

(57) ABSTRACT

Apparatus for controlling the temperature of a reaction mixture held within a reaction container, the apparatus including a radiation source for exposing the reaction container to radiation thereby heating the reaction mixture, a temperature sensor for sensing a temperature indicative of a reaction mixture temperature and a controller for controlling the radiation source in accordance with the reaction mixture temperature to thereby selectively heat the reaction mixture.

32 Claims, 12 Drawing Sheets

(56) References Cited

U.S. PATENT DOCUMENTS

| | | | | |
|---|---|---|---|---|
| 5,075,216 | A | 12/1991 | Innis et al. | |
| 5,079,352 | A | 1/1992 | Gelfand et al. | |
| 5,091,310 | A | 2/1992 | Innis | |
| 5,104,792 | A | 4/1992 | Silver et al. | |
| 5,721,123 | A * | 2/1998 | Hayes et al. | 435/91.1 |
| 5,932,075 | A | 8/1999 | Strauss et al. | |
| 6,284,525 | B1 | 9/2001 | Mathies et al. | |
| 6,413,766 | B2 * | 7/2002 | Landers et al. | 435/286.1 |
| 6,489,111 | B1 | 12/2002 | Takahashi et al. | |
| 6,633,785 | B1 * | 10/2003 | Kasahara et al. | 700/73 |
| 6,783,993 | B1 | 8/2004 | Malmquist | |
| 7,081,226 | B1 | 7/2006 | Wittwer et al. | |
| 2003/0015518 | A1 | 1/2003 | Baker et al. | |
| 2005/0233324 | A1 | 10/2005 | Corbett et al. | |
| 2006/0016801 | A1 | 1/2006 | Kitabayashi et al. | |
| 2006/0142134 | A1 * | 6/2006 | Andersson et al. | 494/14 |
| 2006/0147912 | A1 | 7/2006 | Corbett et al. | |

* cited by examiner

THERMAL CYCLING DEVICE

CROSS REFERENCE TO RELATED APPLICATIONS

This application is a §371 national stage of PCT/AU2008/001752 filed Nov. 27, 2008, which claims priority to Australian Application 2007906569 filed Nov. 30, 2007.

FIELD OF THE INVENTION

The present invention relates to apparatus and a method for controlling the temperature of a reaction mixture and in particular to thermal cycling devices for nucleic acid amplification. However, it will be appreciated that the invention is not limited to this particular field of use.

BACKGROUND OF THE INVENTION

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

PCR is a technique involving multiple cycles that results in the exponential amplification of certain polynucleotide sequences each time a cycle is completed. The technique of PCR is well known and is described in many books, including, PCR: A Practical Approach M. J. McPherson, et al., IRL Press (1991), PCR Protocols: A Guide to Methods and Applications by Innis, et al., Academic Press (1990), and PCR Technology: Principals and Applications for DNA Amplification H. A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584.

The PCR technique typically involves the step of denaturing a polynucleotide, followed by the step of annealing at least a pair of primer oligonucleotides to the denatured polynucleotide, i.e., hybridizing the primer to the denatured polynucleotide template. After the annealing step, an enzyme with polymerase activity catalyzes synthesis of a new polynucleotide strand that incorporates the primer oligonucleotide and uses the original denatured polynucleotide as a synthesis template. This series of steps (denaturation, primer annealing, and primer extension) constitutes a PCR cycle.

As cycles are repeated, the amount of newly synthesized polynucleotide increases exponentially because the newly synthesized polynucleotides from an earlier cycle can serve as templates for synthesis in subsequent cycles. Primer oligonucleotides are typically selected in pairs that can anneal to opposite strands of a given double-stranded polynucleotide sequence so that the region between the two annealing sites is amplified.

Denaturation of DNA typically takes place at around 90 to 95° C., annealing a primer to the denatured DNA is typically performed at around 40 to 60° C., and the step of extending the annealed primers with a polymerase is typically performed at around 70 to 75° C. Therefore, during a PCR cycle the temperature of the reaction mixture must be varied, and varied many times during a multicycle PCR experiment.

The PCR technique has a wide variety of biological applications, including for example, DNA sequence analysis, probe generation, cloning of nucleic acid sequences, site-directed mutagenesis, detection of genetic mutations, diagnoses of viral infections, molecular "fingerprinting" and the monitoring of contaminating microorganisms in biological fluids and other sources.

In addition to PCR, other in vitro amplification procedures, including ligase chain reaction as disclosed in U.S. Pat. No. 4,988,617 to Landegren and Hood, are known and advantageously used in the prior art. More generally, several important methods known in the biotechnology arts, such as nucleic acid hybridization and sequencing, are dependent upon changing the temperature of solutions containing sample molecules in a controlled fashion. Conventional techniques rely on use of individual wells or tubes cycled through different temperature zones. For example, a number of thermal "cyclers" used for DNA amplification and sequencing are disclosed in the prior art in which a temperature controlled element or "block" holds a reaction mixture, and wherein the temperature of the block is varied over time. One advantage of these devices is that a relatively large number of samples can be processed simultaneously, e.g. 96 well plates are commonly employed. However, such devices suffer various drawbacks, in that they are relatively slow in cycling the reaction mixtures, they are relatively energy intensive to operate, temperature control is less than ideal and detection of the reaction mixture in situ is difficult.

In an effort to avoid several of these disadvantages, other thermal cyclers have been developed in which a plurality of containers for holding reaction mixture(s) are supported on a rotatable carousel rotatably mounted within a chamber adapted to be heated and cooled. For example, see U.S. Pat. No. 7,081,226 to Wittwer et al. However, these devices still suffer various disadvantages. For example, control over the temperature of the reaction mixtures is less than ideal, control over the rate of heating and cooling of the reaction mixtures is less than ideal, and these devices have relatively poor energy efficiency.

Thus, there still remains a need for thermocyclers for PCR which provide improved temperature control of the reaction mixtures, are not complex to use, can provide real-time to analysis of the reaction occurring in the sample containers, and are energy efficient.

The present invention seeks to overcome or ameliorate at least one of the disadvantages of the abovementioned prior art, or to provide a useful alternative.

SUMMARY OF THE INVENTION

In a first broad form the present invention seeks to provide apparatus for controlling the temperature of a reaction mixture held within a reaction container, the apparatus including:

a) a radiation source for exposing the reaction container to radiation thereby heating the reaction mixture;
b) a temperature sensor for sensing a temperature indicative of a reaction mixture temperature; and,
c) a controller for controlling the radiation source in accordance with the reaction mixture temperature to thereby selectively heat the reaction mixture.

Typically the apparatus includes a heat source for heating a chamber containing the reaction container.

Typically the controller is for:

a) increasing the temperature of the reaction mixture at least in part using the radiation source; and,
b) maintaining the temperature of the reaction mixture at least in part using the heat source.

Typically the apparatus includes a cooling mechanism for cooling the reaction mixture.

Typically the cooling mechanism is for cooling the reaction mixture from an elevated temperature.

Typically the cooling mechanism supplies ambient air to a chamber containing the reaction container.

Typically the cooling mechanism supplies chilled fluid to a chamber containing the reaction container.

Typically the temperature sensor is an infra-red sensor.

Typically the temperature sensor is an optical sensor for sensing a colour of a temperature dependent indicator in the reaction mixture.

Typically the temperature sensor senses the temperature of the reaction mixture.

Typically the temperature sensor senses a reaction container temperature and wherein the controller is for determining the reaction mixture temperature using the reaction container temperature.

Typically the temperature sensor senses a chamber temperature and wherein the controller is for determining the reaction mixture temperature using the chamber temperature.

Typically the radiation source generates infra-red radiation. Typically the radiation source generates optical radiation.

Typically the apparatus includes a chamber for receiving the reaction containers in use.

Typically the apparatus includes a mounting for receiving a number of reaction containers, the radiation source and mounting being arranged to allow heating of one or more of the number of reaction containers.

Typically the apparatus includes a drive for moving the mounting relative to the radiation source.

Typically the controller is for controlling the drive to thereby selectively heat reaction mixture in respective ones of the number of reaction containers.

Typically the radiation source exposes a heating zone to radiation and wherein the controller controls heating of the reaction mixture by selectively exposing the reaction container to the heating zone.

Typically the controller is a processing system.

Typically the controller is for:

a) increasing the reaction mixture temperature to a first temperature value to denature polynucleotides in the reaction mixture;

b) decreasing the reaction mixture temperature to a second temperature value to anneal polynucleotides in the reaction mixture; and, c) increasing the reaction mixture temperature to a third temperature value to hybridize the denatured polynucleotides.

Typically the controller is for:

a) determining the reaction mixture temperature using signals received from the temperature sensor; and, b) controlling the radiation source based on the reaction mixture temperature, allowing the reaction mixture temperature to be controlled.

Typically the controller is for:

a) controlling the radiation source to increase the reaction mixture temperature to the first temperature value;

b) controlling a heat source to maintain the reaction mixture temperature at the first temperature value;

c) controlling a cooling mechanism to thereby decrease and maintain the reaction mixture temperature at the second temperature; and, d) controlling the radiation source to thereby increase the reaction mixture temperature to the third temperature value; and, e) controlling the heat source to maintain the reaction mixture temperature at the third temperature value.

Typically the radiation source is adapted to selectively generate a predetermined heating zone and wherein the apparatus includes a coolant supply port adapted to selectively generate a predetermined cooling zone, wherein the predetermined heating zone and the predetermined cooling zone are generated substantially adjacent the heater and the coolant supply port respectively, such that the temperature of the reaction mixture is controllable by selective exposure of the reaction container to the heating zone and/or the cooling zone.

Typically the reaction container is at least partially transmissive to the radiation.

Typically the radiation has a wavelength selected in accordance with at least one of reaction container properties and reaction mixture properties.

In a second broad form the present invention seeks to provide a method of controlling the temperature of a reaction mixture held within a reaction container, the method including, in a controller, a) determining a reaction mixture temperature using signals received from a temperature sensor; and, b) controlling a radiation source the radiation source being for exposing the reaction container to radiation thereby heating the reaction mixture; the radiation source being controlled based on the reaction mixture temperature, allowing the reaction mixture temperature to be controlled.

In a third broad form the present invention seeks to provide apparatus for controlling the temperature of a reaction mixture held within a reaction container, the apparatus comprising:

i) a heater adapted to selectively generate a predetermined heating zone and a coolant supply port adapted to selectively generate a predetermined cooling zone, wherein the predetermined heating zone and the predetermined cooling zone are generated substantially adjacent the heater and the coolant supply port respectively, such that the temperature of the reaction mixture is controllable by selective exposure of the reaction container to the heating zone and/or the cooling zone.

Typically the heater is one or more IR emitters.

Typically the coolant supply port comprises a plurality of apertures disposed adjacent the heater, and wherein the coolant is ambient air.

Typically a plurality of reaction containers are provided in an array.

Typically the temperature of the reaction mixture is controllable by selective exposure of the reaction container to the heating zone or the cooling zone according to a predetermined thermal profile.

Typically the predetermined thermal profile is adapted for nucleic acid amplification.

Typically the heating zone and cooling zone are substantially coincident.

In a fourth broad form the present invention seeks to provide a method for controlling the temperature of a reaction mixture held within a reaction container, the method comprising the steps of:

i) providing a heater adapted to selectively generate a predetermined heating zone; and ii) providing a coolant supply port adapted to selectively generate a predetermined cooling zone;

iii) wherein the predetermined heating zone and the predetermined cooling zone are generated substantially adjacent the heater and the coolant supply port respectively; and iv) controlling the temperature of the reaction mixture by selective exposure of the reaction container to the heating zone and/or the cooling zone.

In a fifth broad form the present invention seeks to provide a method for controlling the temperature of a reaction mixture held within a reaction container, the method comprising the steps of:

i) selectively exposing the reaction container to a predetermined heating zone and/or a predetermined cooling zone, wherein the predetermined heating zone and the predetermined cooling zone are generated substantially adjacent a heater and a coolant supply port respectively.

It will be appreciated that the broad forms of the invention may be used individually or in combination, and may be used for temperature control in a range of different applications, including, but not limited to nucleic acid amplification.

BRIEF DESCRIPTION OF THE DRAWINGS

A preferred embodiment of the invention will now be described, by way of example only, with reference to the accompanying drawings in which.

PREFERRED EMBODIMENT OF THE INVENTION

Figure 1:
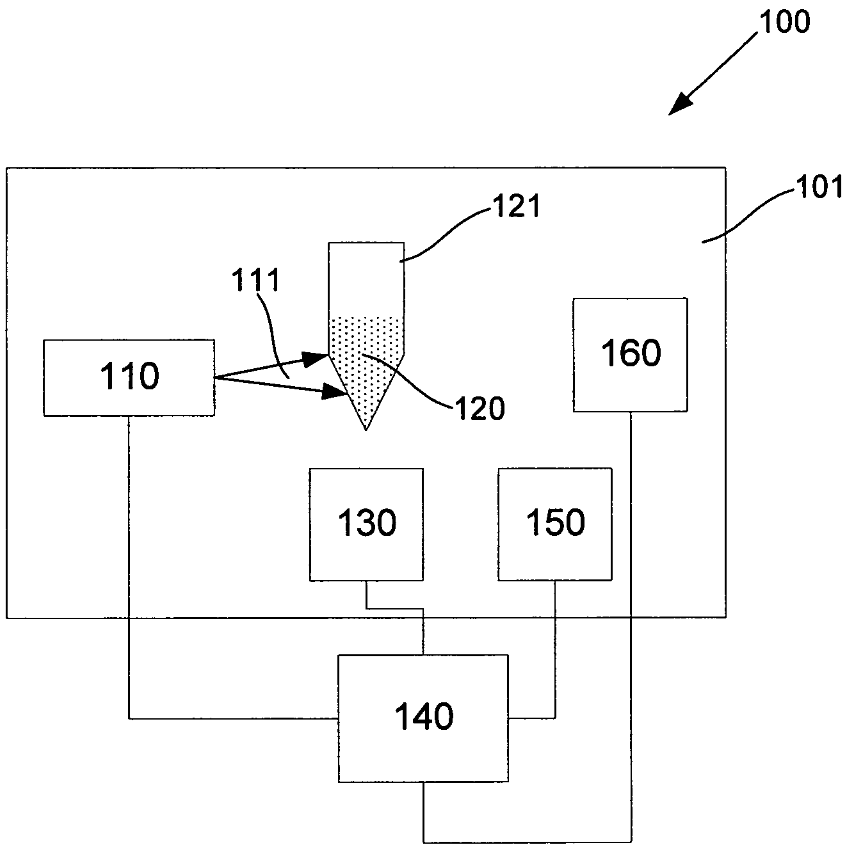
FIG. 1 is a schematic diagram of an example of apparatus for controlling the temperature of a reaction mixture.

References will now be made to the drawings wherein like reference numerals refer to like parts throughout.

An example apparatus for controlling the temperature of a reaction mixture held within a reaction container, will now be described with reference to FIG. 1.

In this example, the apparatus 100 includes a chamber 101 containing a radiation source 110 for exposing a reaction container 121 to radiation thereby heating a reaction mixture 120 provided therein. The radiation source may be any suitable form of radiation source, but is typically in the form of an infra-red heater for generating infra-red radiation. However, in other examples, one or more lasers, light emitting diodes (LEDs), or the like can be used to generate optical or infra-red radiation. The radiation can be used to heat the reaction container, which in turn heats the reaction mixture.

Alternatively the radiation may heat one or more components in the reaction mixture directly, for example, if the reaction containers are at least partially transmissive to the radiation. In this regard, it will be appreciated that the wavelength of the radiation can be selected in accordance with at least one of reaction container properties and reaction mixture properties. Thus, reaction container properties such as the container thickness and material used, as well as reaction mixture properties, such as the mixture constituents, can be used to select a wavelength of radiation so that at least some of the radiation will pass through the reaction container and be absorbed by the reaction mixture. It will be appreciated however, that as an alternative, the reaction container properties, and/or reaction mixture properties can be selected dependent on the wavelength of radiation generated by the radiation source.

The reaction container may be provided in an array coupled to a drive mechanism allowing multiple containers to be moved relative to the radiation source, allowing the reaction containers to be selectively and/or periodically exposed to radiation. This can be used to help control the reaction process, as well as to allow multiple reaction mixtures to be processed simultaneously.

A temperature sensor 130 is positioned in the chamber 101 for sensing a temperature indicative of a reaction mixture temperature. The temperature sensing may be performed in any suitable manner, including using an infra-red sensor, such as a thermopile sensor. Alternatively, the reaction mixture can contain an indicator, such as a dye or other colourant, that has a temperature dependent colour, allowing the temperature to be sensed using an optical sensor. Whilst the temperature of the reaction mixture may be determined directly, a further alternative is to detect the temperature of the reaction container 121. The temperature of air within the chamber 101 could also or alternatively be detected, allowing the reaction mixture temperature to be derived therefrom, for example using a suitable algorithm.

A controller 140 is provided coupled to the temperature sensor 130 and the radiation source 110. In use the controller 140 determines the reaction mixture temperature using signals received from the temperature sensor 130. The controller 140 then controls the radiation source 110 based on the reaction mixture temperature, allowing the reaction mixture temperature to be controlled. Thus, this allows the controller 140 to control thermal cycling of the reaction mixture, for example for use in a nucleic acid amplification process such as PCR.

The controller 140 is therefore adapted to monitor signals from the temperature sensor 130, and control the radiation source 110. Accordingly, the controller can be any suitable form of controller, such as a suitably programmed processing system, FPGA (Field Programmable Gate Array) or the like.

In one example, an additional heat source, such as a convection heater 150, can be used to heat the chamber 101 to assist in increasing and/or maintaining the reaction mixture temperature. The convection heater 150 is typically controlled by the controller 140 based either on the reaction mixture temperature or a temperature of the chamber 101.

In one example, cooling can also be provided by a cooling mechanism 160. This can use ambient air, or a coolant, to cool either the reaction container directly, or the chamber 101, depending on the preferred implementation. The cooling mechanism is typically controlled by the controller 140, based on the reaction mixture temperature or a chamber temperature, to increase the rate of any cooling performed during the temperature control process.

In one example, the use of radiation source to expose the reaction containers to thereby heat the reaction container or reaction mixture directly avoids the need to heat the entire chamber 101. This can reduce the time required to heat the reaction mixture, which can in turn reduce thermal cycle time, and hence the time required to perform a PCR or other amplification processes. This can also reduce the amount of energy required to achieve the reaction mixture temperatures used in performing such processes, thereby reducing overall energy requirements of the apparatus.

In some examples, an additional heat source, such as a convection heater 150, can be used to heat the chamber 101 to assist in maintaining the reaction mixture temperature stability. This can reduce the time taken to achieve the required reaction mixture temperature, whilst allowing a greater reaction mixture temperature stability to be achieved.

The use of a cooling mechanism 160 can also assist in further reducing the temperature cycle time.

In one example, temperature sensing can also be performed on the reaction container or reaction mixture directly. This provides greater accuracy in determining the reaction mixture temperature than may occur, for example, when sensing the temperature of air in the chamber. This increases the accuracy with which the reaction mixture temperature can be controlled, which in turn helps maximise the effectiveness of the amplification process, whilst avoiding the need to implement computationally expensive algorithms to derive the reaction mixture temperature from the chamber air temperature.

Figure 2:
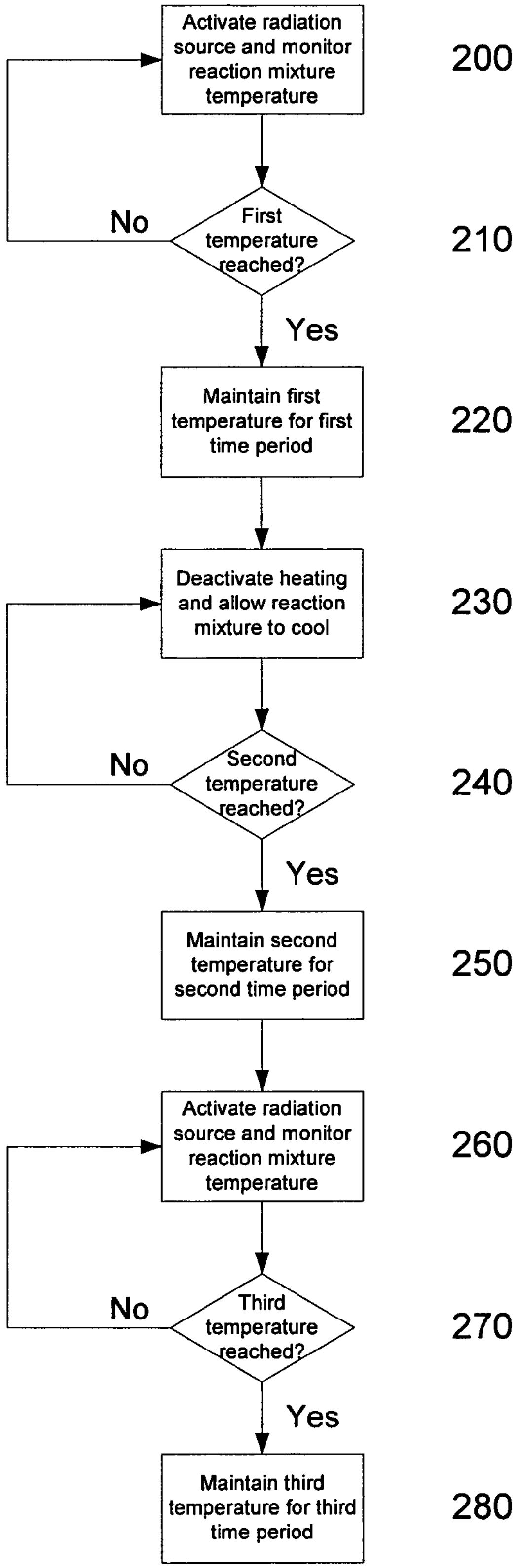
FIG. 2 is a flow chart of an example of a process for controlling the temperature of a reaction mixture using the apparatus of FIG. 1.

An example temperature control cycle will now be described with reference to FIG. 2.

In this example, at step 200, the controller 140 activates the radiation source 110, and monitors the temperature of the reaction mixture using the temperature sensor 130. At step 210 it is determined if the reaction mixture has reached a first temperature, typically around 90° C. to 95° C., and if not the heating process continues at step 200.

Once the first temperature is reached at step 220, the controller 140 controls the heating process to maintain the reaction mixture at the first temperature for a required first time period, such as for 20-30 seconds, thereby allowing denaturating of DNA to occur. It will be appreciated that longer time periods may be used for the first cycle of hot start PCR reactions, such as 1-9 minutes. The time period may be pre-programmed based on the PCR reaction being performed, or may be detected by optical sensing of an indicator on the reaction mixture.

The reaction mixture may be held at the required temperature using any suitable technique. Thus, in one example, the controller 140 can control the amount of radiation generated by the radiation source 110. Additionally or alternatively, a heat source 150, such as a convection heater, may be used.

Once the denaturing step has been completed, the reaction mixture temperature is cooled to a second temperature value, typically 40° C. to 60° C. The cooling process typically involves having the controller 140 deactivate the radiation source 110 and/or convection heater 150 at step 230, allowing the reaction mixture to cool, with the controller 140 monitoring the temperature of the reaction mixture using the temperature sensor 130. A cooling mechanism 160 may also be used to speed up the cooling process. At step 240 it is determined if the reaction mixture has reached the second temperature, and if not the cooling process continues at step 230.

Once the second temperature is reached at step 250, the controller 140 controls the radiation source 110 to maintain the reaction mixture at the second temperature for a required second time period, typically 20-40 seconds, thereby allowing annealing of DNA to a primer to occur. Again, the reaction mixture may be held at the required temperature using any suitable technique, and the time period may be pre-programmed or detected.

Following this, the reaction mixture temperature is heated to a third temperature value by having the controller 140 activate the radiation source 110, and monitors the temperature of the reaction mixture using the temperature sensor 130 at step 260. At step 270 it is determined if the reaction mixture has reached the third temperature, typically around 70° C. to 75° C., and if not the heating process continues at step 260. Once the third temperature is reached, at step 280, the controller 140 maintains the reaction mixture at the third temperature for a third time period thereby performing elongation of the DNA. The third time period will, depend on factors such as the DNA polymerase used and may again be detected or pre-programmed.

It will be appreciated that this is an example of a single cycle, and that in practice a number of cycles, and optional final holding steps would be used to perform a PCR or other amplification process.

Figure 3A:
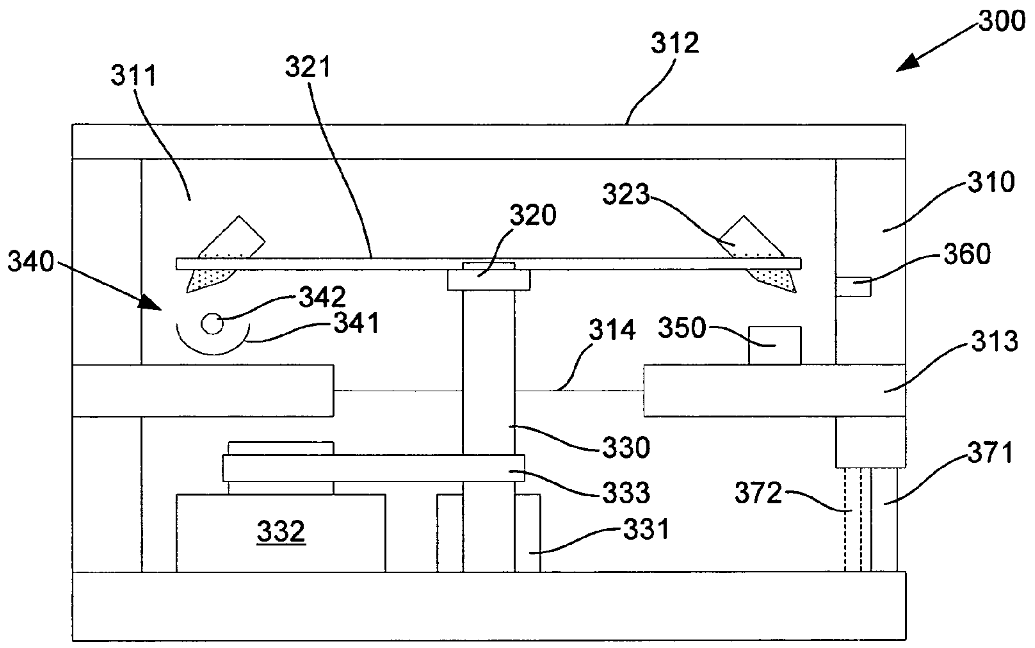
FIG. 3A is a schematic side view of a second example of apparatus for controlling the temperature of a reaction mixture.

An example of apparatus for controlling the temperature of a reaction process will now be described with reference to FIG. 3.

In this example, the apparatus 300 includes a body 310 and cover 312, defining a chamber 311. The chamber 311 includes a mounting 320, for receiving a carousel 321. The carousel 321 includes a number of apertures 322 for receiving reaction containers 323, containing the reaction mixture.

The mounting 320 is coupled to shaft 330, which is rotatably mounted in a bearing 331. A drive motor 332 is coupled to the shaft 330 for example by a drive belt 333, allowing the carousel 321 to be rotated within the chamber 311. A wall 313 is provided that extends across the chamber 311 to separate the drive motor 332 and bearing 331 from the carousel 321. The wall 313 typically includes an aperture having a mesh 314 therein for allowing air flow through the mesh 314.

The chamber 311 includes a radiation source in the form of an IR heater 340 typically mounted to the wall 313. In one example, the heater 340 includes a trough 341 and a conductor 342. In use, a current passing through the conductor 342 causes heating of the conductor 342, which in turn generates infra-red radiation that is emitted from the surface of the conductor 342. The trough then reflects the radiation so that the radiation impinges on the reaction containers 323.

In this example, an optical sensor 350 is also provided mounted to the wall 313, to sense the status of the reaction based on the colour of an indicator in the reaction mixture. The optical sensor 350 can include an illumination source, such as a laser, and a corresponding optical detector for detecting reflected illumination.

Figure 3B:
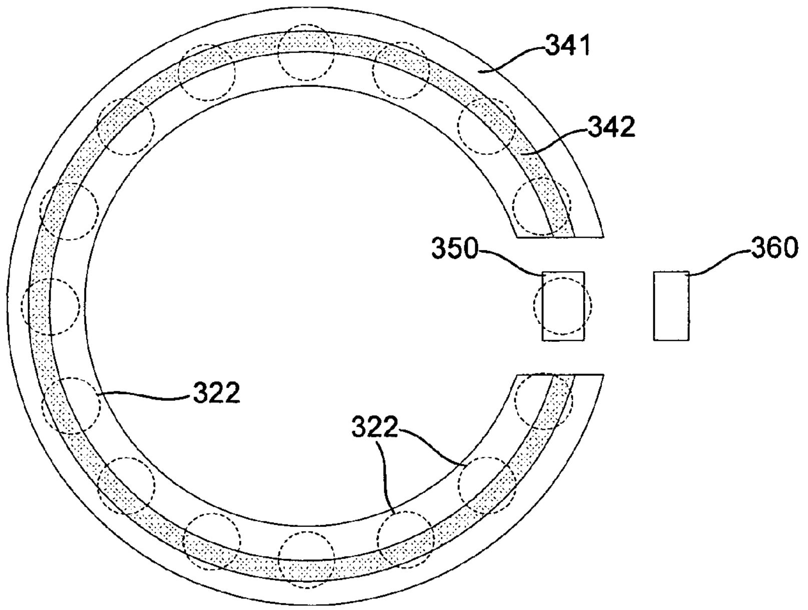
FIG. 3B is a schematic plan view of part of the apparatus of FIG. 3B.

As shown in FIG. 3B, due to positioning of the optical sensor, in one example, the IR heater 340 may extend around only part of the perimeter of the carousel 321, allowing line of sight to be maintained between the optical sensor 350 and the reaction containers 323. However, this is not essential and an alternative position for the optical sensor 350 may be used, as shown at 360, allowing the heater 340 to extend around the entire perimeter of the carousel 321.

Having the heater 340 extend only partially around the perimeter of the carousel 321 can provide advantages. For example, this provides heating over only a portion of the perimeter of the carousel 321 allows reaction containers to be heated for only part of the carousel 321 rotation, which can assist in temperature stabilisation. However, in other examples, more even heating can be achieved using a heater that extends around the entire carousel 321.

In one example, the optical sensor 350 acts as a temperature sensor by detecting the colour of a temperature sensitive indicator agent in the reaction mixture. A temperature dependent indicator may alternatively be incorporated into the reaction container, for example, using a temperature dependent material applied thereto, or actually incorporated into the reaction container material. It will be appreciated that using the optical sensor to sense the reaction mixture or reaction container temperature avoids the need for an additional sensor. This reduces the complexity and overall cost of the apparatus.

Alternatively, an additional temperature sensor may be provided, for example as shown at 360. This can be in the form of an IR sensor, in which case the IR sensor is positioned to detect the temperature of the reaction mixture or reaction container, whilst avoiding detecting radiation emitted from the IR heater 330.

It is additionally, or alternatively possible to sense the air chamber temperature, using an appropriate sensor (not shown). However, this is not generally as sensitive or accurate as detecting the temperature of the reaction chamber or mixture directly, which can reduce the effectiveness of the temperature control.

The chamber 311 includes a fan 371 to allow ambient air from outside the chamber 311 to be circulated through the chamber 311. In one example, a heat source 372 may also be provided for heating the ambient air prior to the air entering the chamber, to thereby provide convective heating of the reaction chamber.

Figure 4:
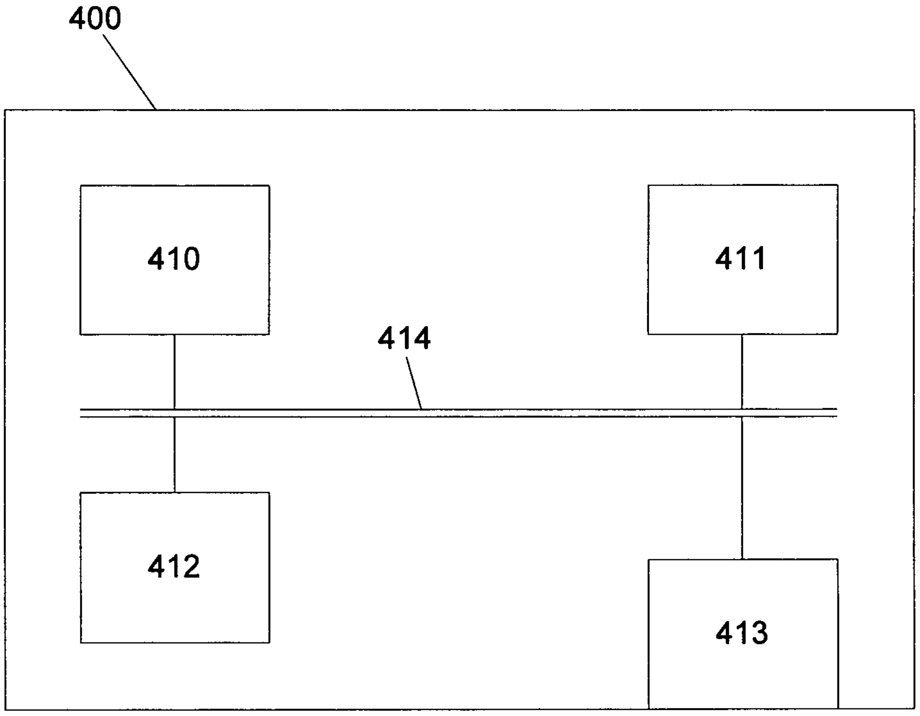
FIG. 4 is a schematic diagram of an example of a controller.
Figure 5:
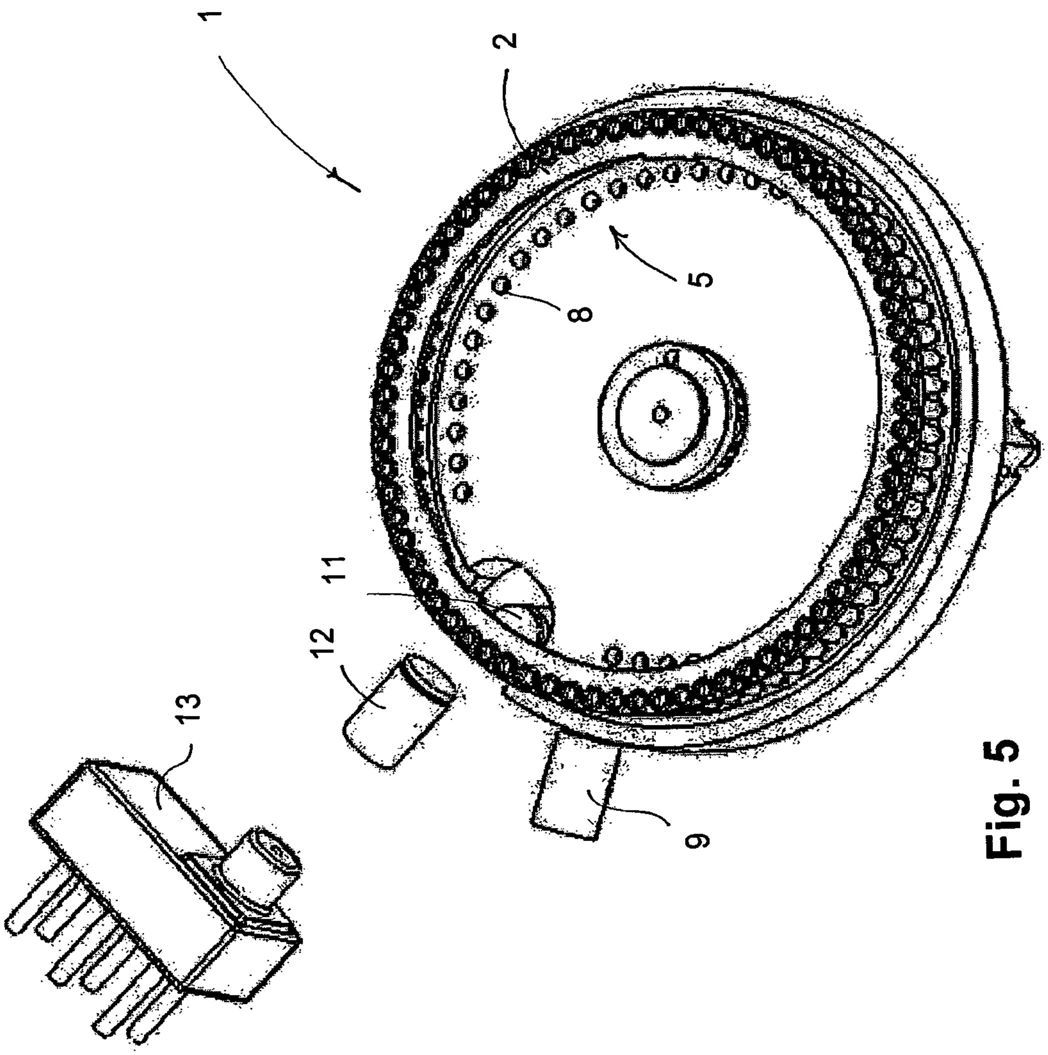
FIG. 5 is a perspective top view of a third example of apparatus for controlling the temperature of a reaction mixture, showing a rotatable carousel supporting a plurality of reaction containers positioned above an IR heater and a plurality of cooling ports.
Figure 6:
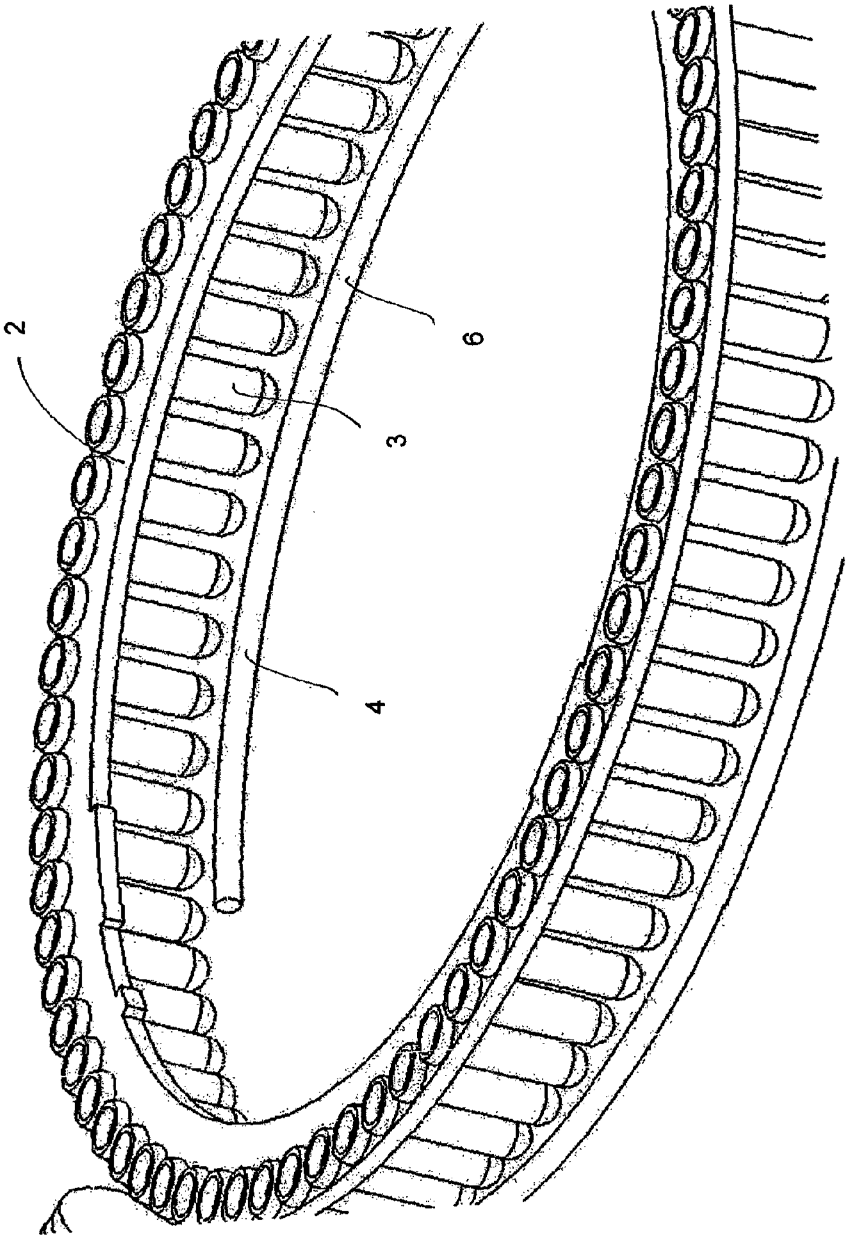
FIG. 6 is a perspective top view of the rotatable carousel and IR heater shown in FIG. 1.

It will be appreciated that the apparatus will also typically include a controller, an example of which will now be described with reference to FIG. 4.

In this example, the controller 400 includes a processor 410, a memory 411, an input/output device 412 such as a keypad and display, and an interface 413 coupled together via a bus 414. The interface 413 may be provided to allow the controller 400 to be coupled to any one or more of the heater 340, the drive 332, the sensors 350, 360, the fan 371 and the heat source 372. The interface may also include an external interface used to provide connection to external peripheral devices, such as a bar code scanner, computer system, or the like. Accordingly, it will be appreciated that the controller 400 may be formed from any suitable processing system, FPGA, or the like.

In use, the processor 410 typically executes instructions, such as software instructions stored in the memory 411, to determine a thermal cycling process to be performed. This may be achieved by accessing preset thermal profiles stored in the memory 411 and/or through the use of input commands supplied via the input device.

The processor 410 then generates control signals to control operation of the heater 340, the drive 332, and optionally the fan 371 or the heat source 372, to commence a thermal cycling process. During this process, the processor 410 receives signals from one or more of the sensors 350, 360, and uses this to determine reaction mixture temperature, typically by using information stored in the memory 411 to interpret the signals. The processor 410 may also determine a reaction status, for example using signals determined from the optical sensor 350.

The processor 410 uses the reaction mixture temperature and optionally the reaction status as feedback to control operation of the heater 340, the drive 332, and optionally the fan 371 or the heat source 372, thereby allowing a thermal cycling process to be implemented substantially as described above with respect to FIG. 2.

A further example apparatus will now be described with reference to the FIGS. 5 to 12, which show apparatus 1 for controlling the temperature of a reaction mixture for nucleic acid amplification.

A rotatable carousel 2 is provided for supporting a plurality of reaction containers 3 for holding a plurality of reaction mixtures (not shown). The reaction containers 3 are preferably formed from plastics materials and are adapted for relatively rapid thermal equilibration and to allow for detection of the reaction mixture. The reaction containers 3 may be charged with any reaction mixture, however in the embodiments contemplated herein the reaction mixtures are for nucleic acid amplification and thermocycler apparatus 1 is configured accordingly, i.e. thermal cycling routine is particularly adapted for nucleic acid amplification according to a predetermined thermal cycling profile as discussed below.

At least one heater 4 is provided for supplying heat to the reaction containers 3, and at least one coolant supply port 5 is provided for supplying coolant to the reaction containers 3. The heater 4 and the coolant supply port 5 are adapted to selectively generate a predetermined heating zone and a predetermined cooling zone respectively. These zones are generated substantially adjacent the heater 4 and the coolant supply port 5 respectively, such that the temperature of the reaction mixture is controllable by selective exposure of the reaction containers 3 to the heating zone and/or the cooling zone. The "predetermined zones" which are generated may be defined as a relatively limited or confined area or region in space, which are heated/cooled. Therefore, introduction of the reaction containers 3 into the zones, or exposure of the reaction containers 3 to the zones, heats/cools the reaction containers 3 in preference to heating/cooling the entire chamber (not shown) in which the apparatus 1 is housed.

The apparatus 1 is able to more rapidly cycle the reaction mixtures compared to prior art devices, thereby reducing the time required to perform amplifications. Moreover, not only can cycle times be reduced but also the degree of control over the reaction temperature may improved compared to prior art devices, since only the reaction mixture is heated and cooled. This is further improved by detecting the actual temperature of the reaction mixture in real-time and providing feedback to a control loop for controlling the amount of heat provided by the heater 4 and the amount of coolant supplied to the reaction containers by the coolant supply port 5. Further improvements are contemplated by measuring the actual course of the reaction occurring in the reaction containers 3, and using the course of the reaction as a control signal for controlling the amount of heat and the amount of coolant supplied to the reaction containers 3.

The heater 4 is preferably in the form of a non-contact heater, such as an infrared (IR) heater/emitter 6, which is conveniently located at the bottom of the chamber housing the rotatable carousel 2 and in close proximity to the rotating reaction containers 3. The IR heater 6 is preferably a stainless steel tube with an outer diameter of approximately 2 mm and an internal diameter of 1.5 mm. The IR heater 6 is preferably circular with a diameter similar to that of the rotatable carousel 2. It will be appreciated that the IR heater 6 should be adapted to supply heat to the reaction containers 3 such that essentially a localised zone about the reaction container 3 is heated. A parabolic reflector 7 is also preferably provided. The reflector 7 is preferably adapted to substantially focus the heat provided by the IR heater 6 onto the reaction containers 3.

Figure 7:
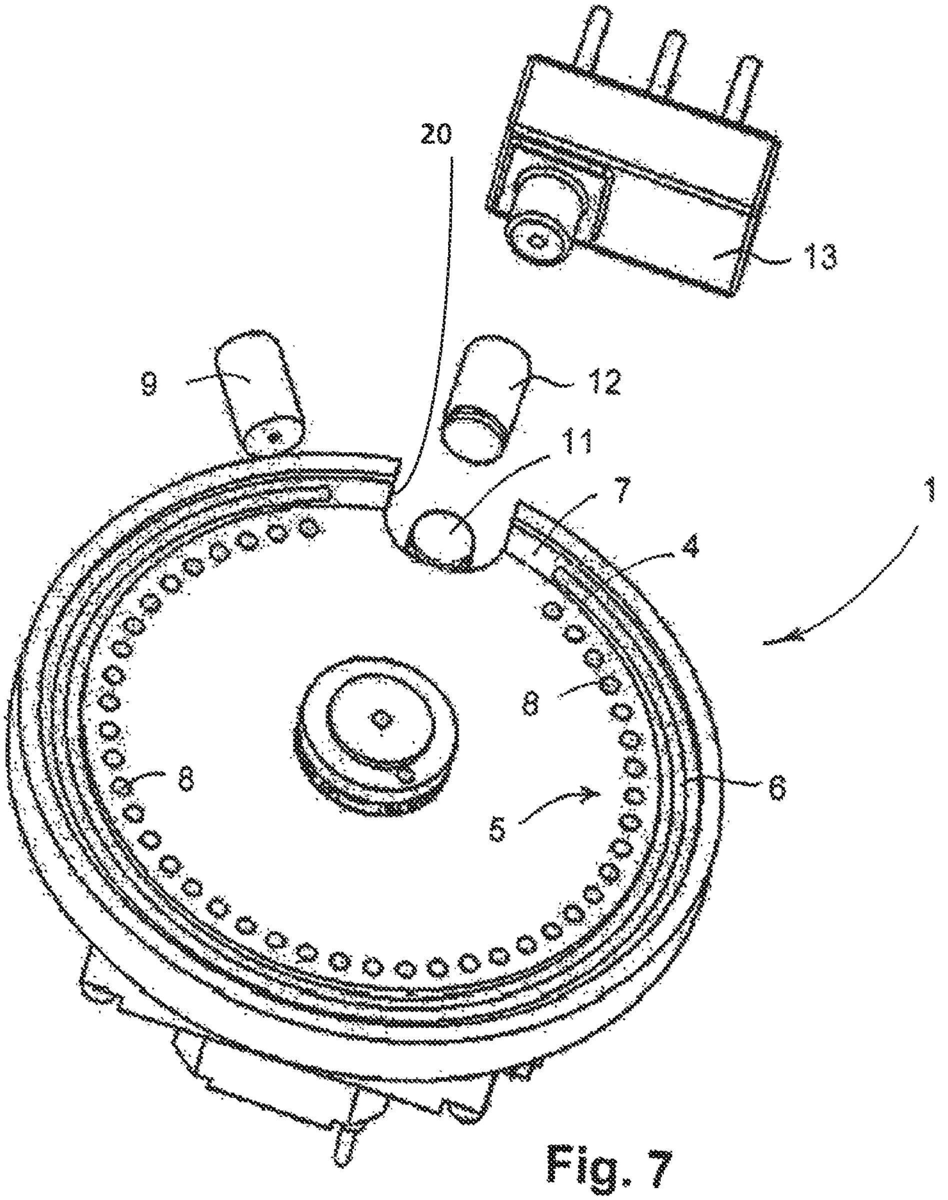
FIG. 7 is a perspective top view of an example of a base plate having the IR heater/reflector arrangement and cooling ports.
Figure 8:
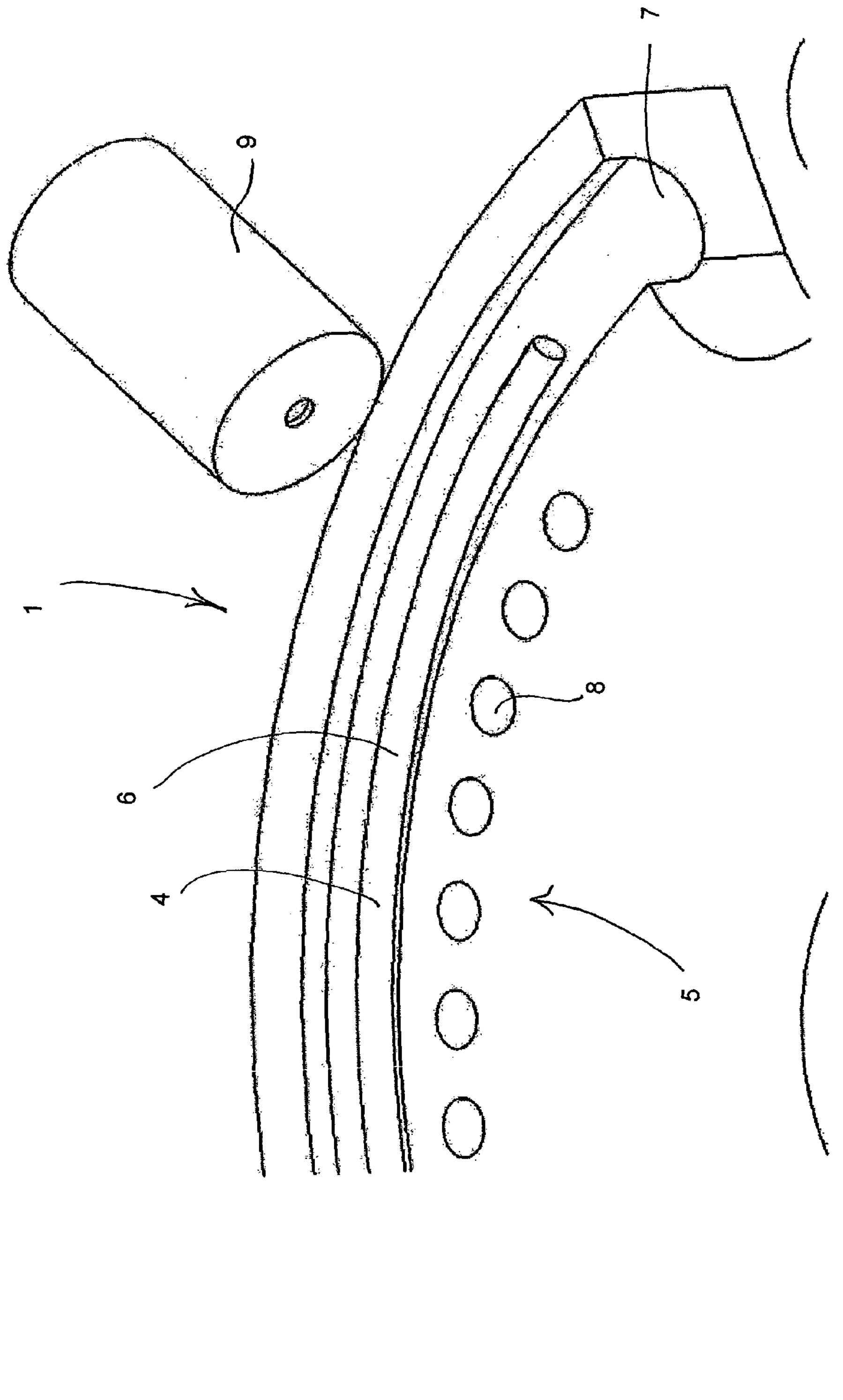
FIG. 8 is a close-up view of a portion of FIG. 7 showing a non-contact temperature sensor disposed adjacent the IR heater/reflector.
Figure 9:
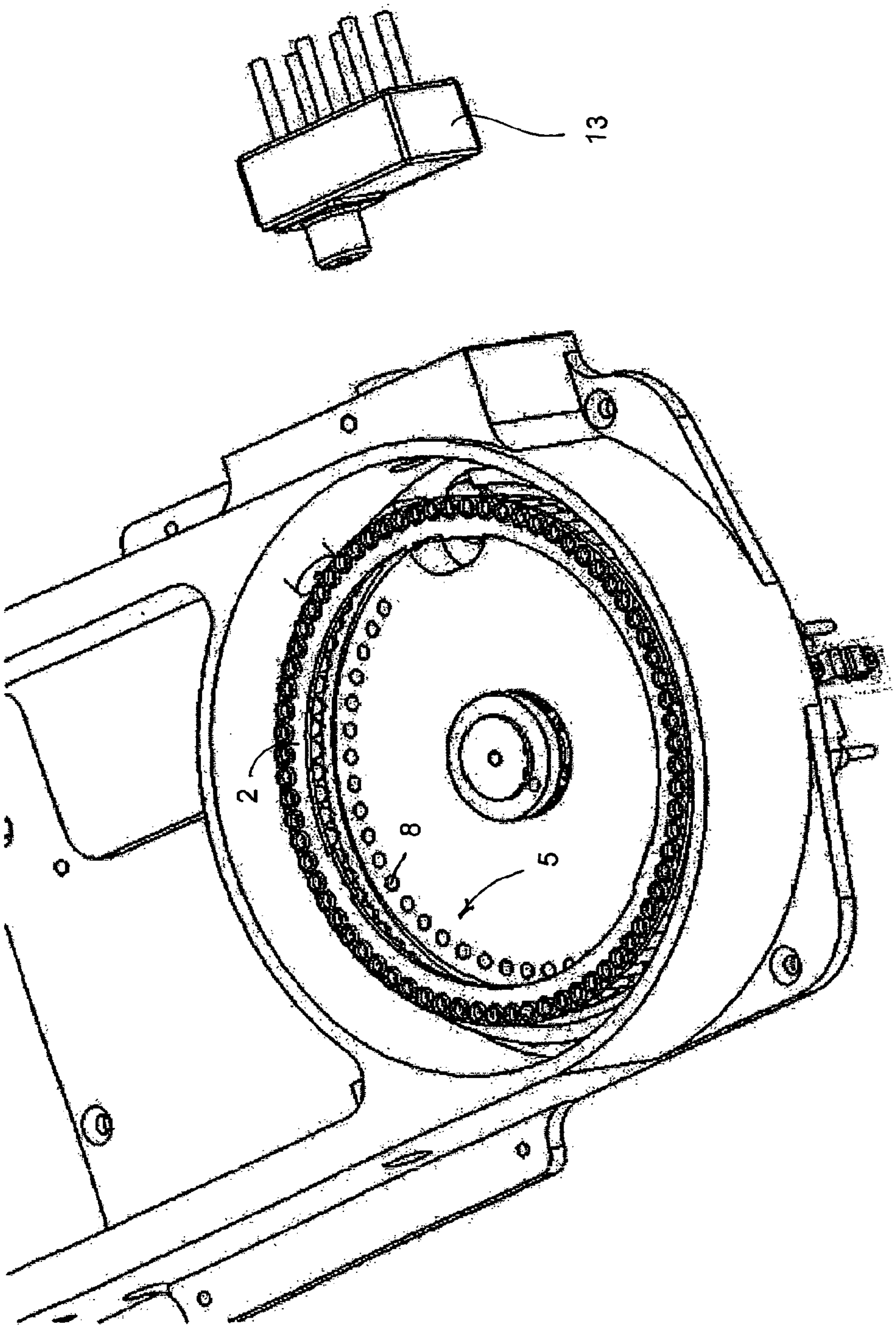
FIG. 9 shows the apparatus as shown in FIG. 7 disposed in a housing.
Figure 10:
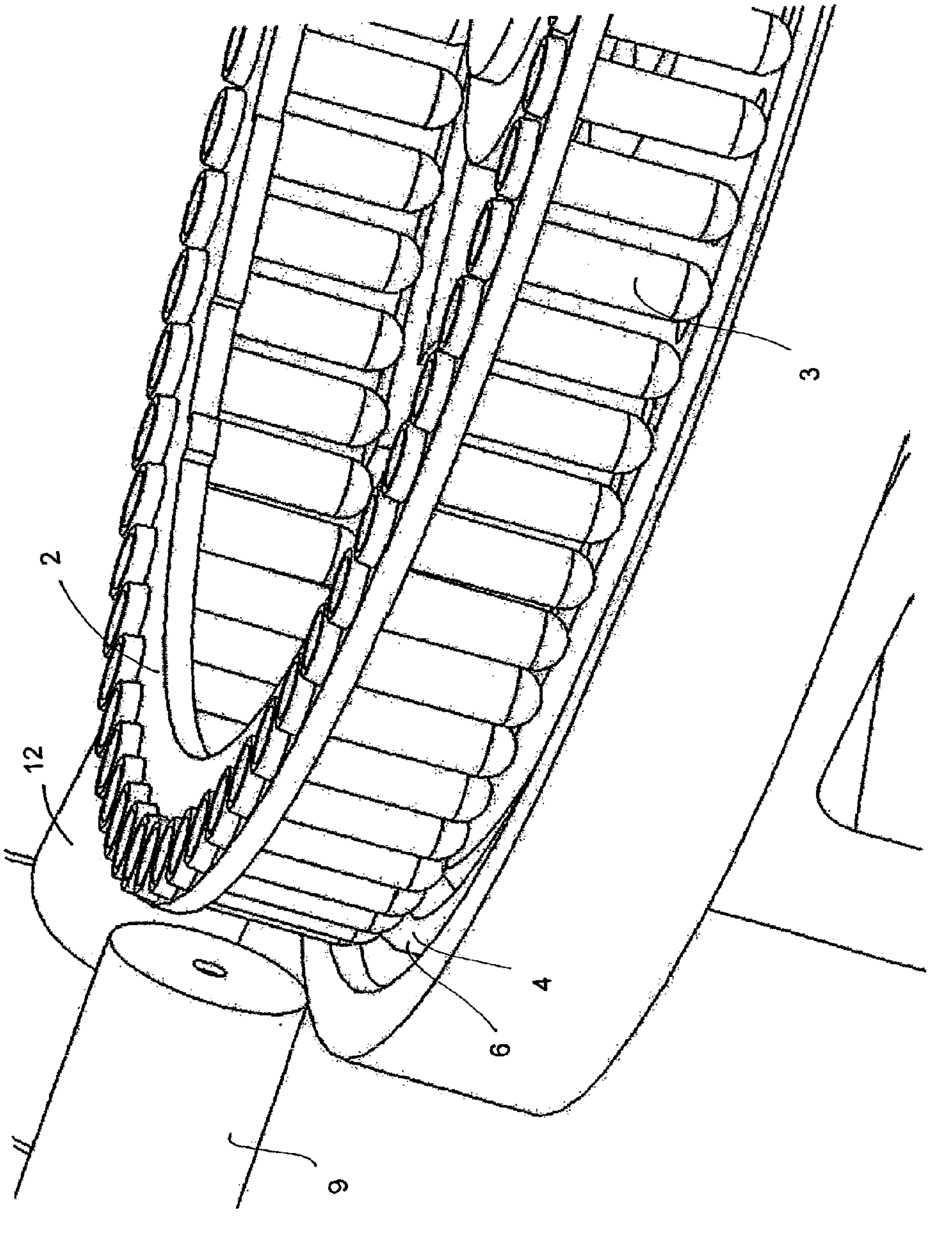
FIG. 10 is a view similar to FIG. 8 and also showing the reaction containers.
Figure 11:
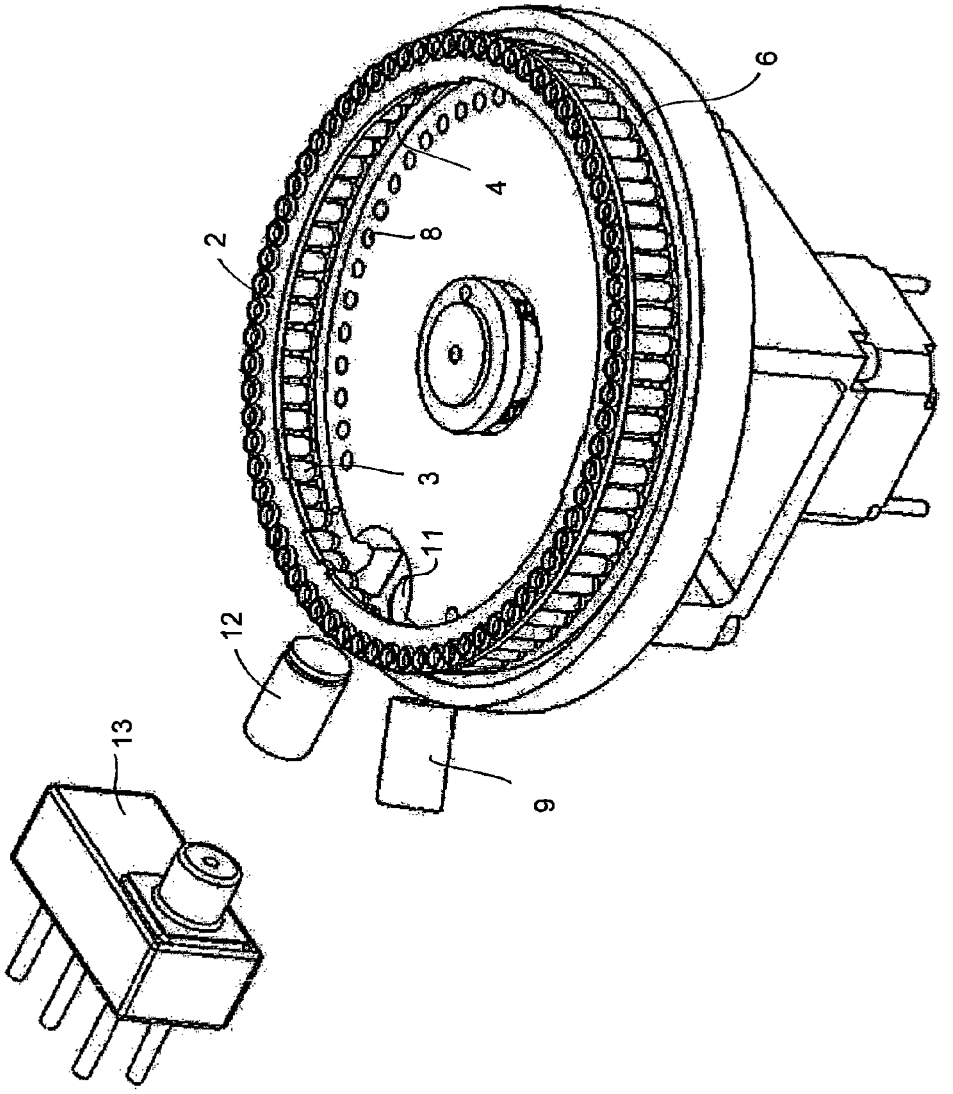
FIG. 11 is a view similar to FIG. 5.
Figure 12:
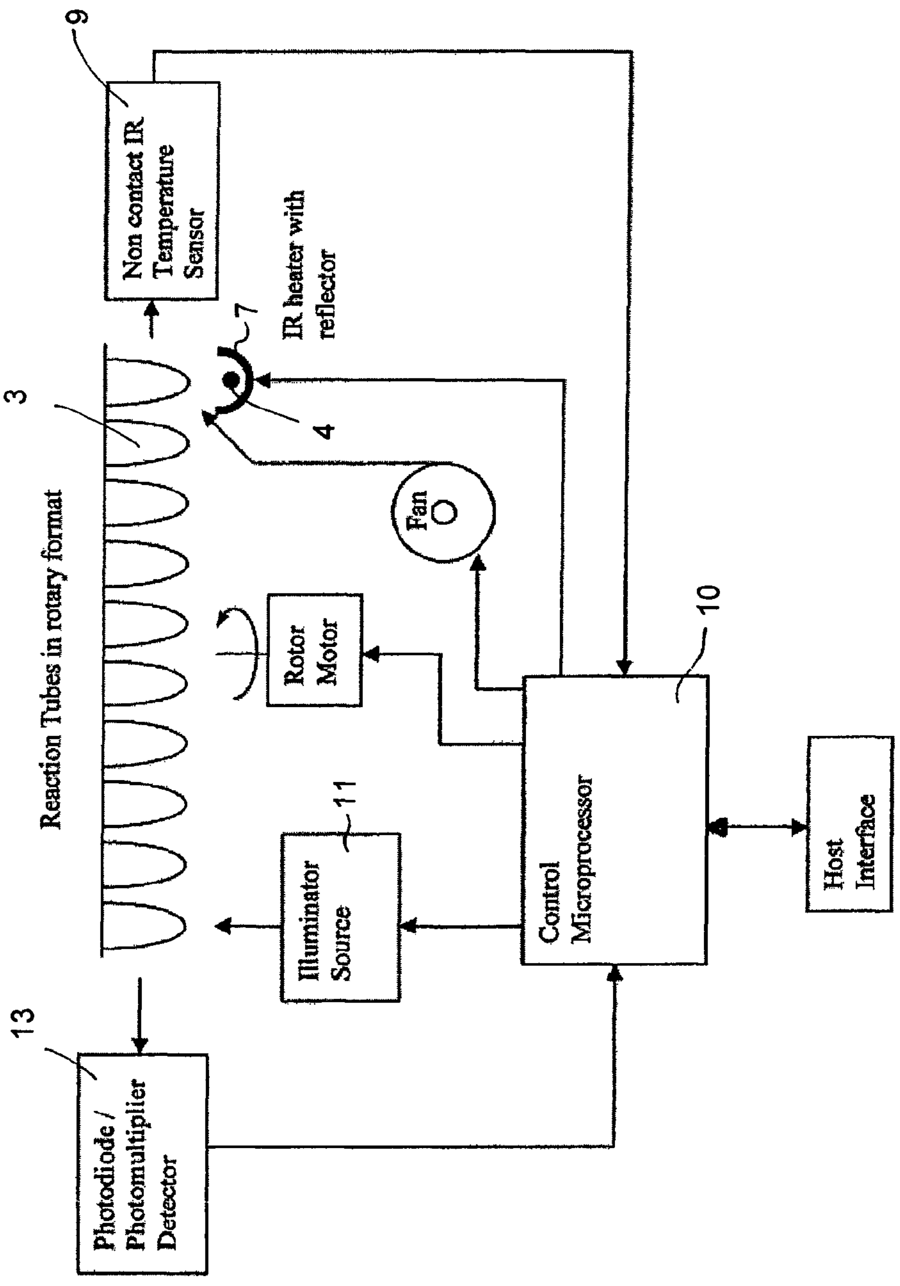
FIG. 12 is a schematic diagram of an example of the components of apparatus for controlling the temperature of a reaction mixture.

The coolant supply port 5 may be an annular slot disposed adjacent the reflector plate 7. However, in other examples, the coolant supply port 5 comprises a plurality of circumferentially spaced apertures 8 disposed adjacent the reflector plate. In FIG. 7, for example, a base plate 20 comprises i) the coolant supply port 5 comprising a plurality of circumferentially spaced apertures 8 and ii) the reflector plate 7 to which the plurality of circumferentially spaced apertures 8 are adjacent. The coolant supply apertures 8 are preferably adapted to impinge the coolant directly onto the reaction containers 3. In this way a localized zone of cooling is established about the reaction containers 3. Preferably the coolant is ambient air, however, the ambient air may be pre-chilled.

The temperature of the reaction containers 3 may be measured/sensed during a thermal cycling experiment, preferably by way of a thermopile detector 9. The measured temperature of the reaction containers may be fed back to a control loop, such as a Proportional-Integral-Derivative (PID)-type controller coded into a control microprocessor 10, which can adjust the amount of heat or the amount of coolant supplied to the containers 3. It will be appreciated that not only can the temperature of the reaction containers 3 be measured/sensed during a thermal cycling experiment, but the progress of the reaction(s) occurring in the reaction containers 3 may also be monitored. The monitoring may be by any means, however one preferred example is by use of a fluorescent probe which is included in the reaction mixture.

The monitoring is preferably by way of a light source 11, filter 12, and photomultiplier tube 13. Results of the progress of the reaction can also be recorded by the control microprocessor 10. It will be appreciated that the progress of the reactions occurring in the reaction containers 3 may be used as the control signal to increase or lower the temperature of the reaction containers to increase or reduce the extent of the reactions occurring in the reaction containers 3.

A number of further features for use in, or with the above examples will now be described.

In one example, the temperature of the reaction mixture is controllable according to a predetermined thermal profile. This allows the reaction mixture to be used for nucleic acid amplification and the predetermined thermal profile is adapted for nucleic acid amplification.

The thermal profile may be pre-stored in the controller or memory, and may be selected from a number of profiles via appropriate commands provided via an input device. Alternatively, the profile may be input manually using the input device.

In one example, a plurality of reaction containers are provided in an array, such as a rotatable carousel. Each reaction container may contain the same or different reaction mixtures, allowing a plurality of reaction mixtures to be processed simultaneously.

The heater is typically one or more IR emitters, and the coolant supply port comprises a plurality of apertures disposed adjacent the IR emitter(s). In one example the heater is an IR emitter supplying IR energy which is absorbed by the reaction container and its contents, causing them to heat. In such examples, the heating zone and cooling zone are substantially coincident.

In one example, the "predetermined zone" is achieved by the supply of heat or coolant to a relatively limited or confined area or region in space. This is in contrast with prior art devices which heat/cool the entire chamber within which the reaction containers are housed. By focussing or concentration of heat/coolant within a predetermined localised zone in an ambient space into which the reaction container may be introduced/exposed thereby heating and/or cooling the reaction container and its contents. In some embodiments just the tip of the reaction container is heated/cooled by introducing just the tip of the reaction container into the zones, and in other embodiments the lower half of the reaction container may be heated/cooled.

However, it will be appreciated that the heating means, in the form of an IR heater/emitter, and the cooling means, in the form of a coolant supply port, may be adapted to heat/cool the entire reaction container without substantially heating/cooling the entire chamber housing the reaction containers. A certain degree some heating/cooling of the chamber per se may result. However, the technique minimises any "waste" heating/cooling of the chamber by thermally affecting just the localised environment surrounding the reaction containers.

A number of advantages can be achieved by heating and cooling the reaction mixture, or the reaction containers, or a portion thereof, as opposed to the entire chamber housing the reaction containers, as is common in many prior art devices. For example, the technique can provide heating and/or cooling times which are typically faster than prior art devices which heat the entire chamber. Clearly, it is advantageous to be able to more rapidly cycle the reaction mixtures, thereby reducing the time required to perform amplifications.

Additionally, the heating and/or cooling the reaction mixture more directly can increase the degree of control over the reaction temperature may improved compared to prior art devices, since only the reaction mixture or reaction container is heated and cooled. Additionally, the actual temperature of the reaction mixture or reaction container can be rapidly detected providing feedback to the control loop. This is in contrast with prior art devices which flood the chamber with heating and cooling fluid and do not use the actual temperature of the reaction mixture as a feedback element.

The apparatus can also provide fine temperature control of the reaction mixtures being thermally cycled in the reaction containers. This is a significant advance over prior art devices which can only relatively coarsely control the reaction temperature over comparative cycle times since typically such prior art devices are effectively "open loop" where air or block temperature is controlled only; the actual temperature of the reaction mixture is not used as the primary feedback element in thermal control loop.

Furthermore, improvements in energy efficiency can be realised since there is minimal wastage of heat and cooling fluid. Also, relatively smaller heating and cooling means can be used compared to prior art devices since the entire chamber does not need to be heated and cooled, meaning reduced cost for fabrication of the instrument.

Many other advantages may also be achieved. For example, the chamber housing the rotatable carousel can use very little or no insulation, since there is minimal wastage of heat/coolant, and a fluid circulation fan can be avoided to circulate the heated/cooled air around the reaction containers and throughout the chamber, if cooling ports are used.

The apparatus is particularly directed to thermocyclers for nucleic acid amplification, wherein the reaction containers are supported on a rotatable circular carousel rotatably mounted within a chamber. Particularly preferred thermocyclers for use with the apparatus are the Rotor-Gene™ family of thermocyclers manufactured and distributed by Corbett Life Sciences Pty Limited (www.corbettlifescience.com). Other similar devices are disclosed in International PCT Publication No.'s WO 92/20778 and WO 98/49340. However, it will be appreciated that other commercially available thermocyclers may be modified to operate as described above.

Rotation of the reaction containers can provide a number of advantages. For example, one of the main advantages lies in being able to monitor the course of the amplification reaction in situ. Since the rotatable carousel is typically circular, preferably the heater and the coolant supply port are also circular such that the reaction containers experience a constant heat or a constant cooling during rotation. In this case, rotation of the carousel means that there is no need to position the reaction containers over a particular heating/cooling zone to heat/cool the containers.

In some examples, the coolant supply port can be radially inwards or radially outwards of the heater. It will also be appreciated that the heater (or coolant supply port) could be one or more sectors of a circle such that the reaction containers experience intermittent heating (or cooling) as they are spun. However, in alternative embodiments the heater and coolant supply port may be sectors of a circle which are alternated to define alternating heating/cooling zones.

In one example, a non-contact heater can be used to cause heating of the reaction mixture. For example, a suitable heating source is a microwave emitter, or in preferred embodiments, an infrared (IR) heater. In the case of an IR heater, the heater is preferably capable of delivering at least 100 Watts. In one example, a preferred IR heater is a stainless steel tube with an outer diameter of approximately 2 mm and an internal diameter of 1.5 mm.

Alternatively, the IR heater is a Ni-Chrome element wound in a spiral configuration about a tube.

The IR heater can be located at the bottom of the chamber housing the rotatable carousel and in close proximity to the rotating reaction containers. In one example the IR heater is subjacent the reaction containers such that the reaction containers overlie the IR heater in use.

However, in alternative examples, it will be appreciated that the IR heater could be positioned radially outward (or inward) from the reaction containers and adapted to direct the IR energy radially inwards (or outwards) towards the reaction containers supported on the rotatable carousel.

Irrespective of the actual configuration the heater can be adapted to supply heat to the reaction containers or reaction mixture so that at most only a localised zone about the reaction container is heated. In one example, the stainless steel tube is mounted on ceramic insulators that are affixed to a reflector plate, the configuration being such that the IR heat generated by the heater is primarily directed towards the reaction containers.

In other examples, the reflector plate is adapted to substantially focus the heat provided by the IR heater onto the reaction container. In such examples, the reflector plate is curved in cross section, and preferably parabolic in cross section. Whilst use of a reflector plate is preferred it will be appreciated that the reflector plate is not essential.

In one example, the coolant supply port is an annular slot disposed adjacent the reflector plate/IR heater arrangement. However, in other examples, the coolant supply port comprises a plurality of circumferentially spaced apertures disposed adjacent the reflector plate/IR heater arrangement. The coolant supply ports can be adapted to impinge the coolant directly onto the reaction containers. In this way a predetermined zone of cooling is established about the reaction container.

In one example, the coolant is ambient air. However the coolant may be any fluid, as is well known in the art. In a related aspect, the coolant is ambient air that has been prechilled. It will be appreciated that the air can be chilled by any means, for example, by flowing the air past the cold-side of a Peltier block prior to impinging the chilled air onto the reaction containers. However, in some preferred examples, the coolant is cooled by adiabatic expansion, as is well known in the art. For example, the coolant supply port could be configured with a source of compressed gas and wherein the coolant supply port takes the form of one or more injector nozzles.

Example reaction containers are adapted for relatively rapid thermal equilibration and to allow for detection of the reaction mixture, and may be formed from glass or plastics materials. In one example, the reaction containers are similar to Eppendorf™ tubes. The reaction containers may be charged with any reaction mixture, however in the embodiments contemplated herein the reaction mixtures are for nucleic acid amplification and thermocycler configured accordingly, i.e. thermal cycling routine is particularly adapted for nucleic acid amplification as discussed above.

In one example, the reaction container is at least partially transmissive to the radiation so that the reaction mixture is at least partially exposed to the radiation, thereby undergoing direct heating. However, alternatively, the reaction container can absorb the radiation and be heated, with heat being conducted to the reaction mixture contained therein.

In one example, the temperature of the reaction container is measured/sensed during a thermal cycling experiment. The temperature sensing means may take any form, as is well known in the art, however preferred temperature sensing means are non-contact sensors. For example, thermopile detectors and similar technologies. By use of suitable reaction containers that are adapted for rapid thermal equilibrium, the reaction mixture held in the reaction container is at the same temperature as the surface of the reaction container. No thermal equilibration is therefore required once a set point is reached. Also thermal equilibration time is no longer dependant upon surface area to volume ratios of the reaction vessels. As the IR is focused on the reaction mixture the rate of heating is proportional to the power delivered to the IR heater and not dependant on the tube geometry as in other conduction (block) and convection (air) thermal cycling systems.

In one example, the temperature of the reaction mixture is sensed directly, for example if the reaction container is transmissive to the radiation used in the sensing, as may occur when optically detecting the colour of an indicator in the reaction mixture.

It will also be appreciated that by only locally heating and cooling the reaction mixture, upon heating to 95° C. at least a portion of the reaction mixture will evaporate and condense on the cold portions of the reaction vessel that have not been exposed to the IR radiation. To overcome this, the rotor is spun at high speed during the cooling cycle to spin down any reaction mixture that may have evaporated during the heating step. Another way to overcome this phenomenon is to overlay the reaction mixture with oil or wax to act as an evaporation barrier.

It will be appreciated that the heater supplying the heat to the reaction container and the cooling port supplying coolant to the reaction container may be operated sequentially or simultaneously, as is well known in the art. For example, when operated sequentially, the temperature control may be considered to be "on/off" control, and when operated simultaneously the temperature control may be considered to be "proportional" control. In the latter case a Proportional-Integral-Derivative (PID)-type controller may be used to control the reaction container temperature.

In one example, a method for controlling a reaction mixture temperature includes the steps of: providing a heater adapted to selectively generate a predetermined heating zone; and providing a coolant supply port adapted to selectively generate a predetermined cooling zone; wherein the predetermined heating zone and the predetermined cooling zone are generated substantially adjacent the heater and the coolant supply port respectively; and controlling the temperature of the reaction mixture by selective exposure of the reaction container to the heating zone and/or the cooling zone.

In another example, a method for controlling a reaction mixture temperature includes the steps of: selectively exposing the reaction container to a predetermined heating zone and/or a predetermined cooling zone, wherein the predetermined heating zone and the predetermined cooling zone are generated substantially adjacent a heater and a coolant supply port respectively.

In such examples, this can be used to allow the reaction container to be heated/cooled without heating/cooling the entire chamber housing the reaction containers, such as is typical with prior art devices. This reduces the amount of energy required to heat and cool the reaction mixture, and can also reduce the heating time, as previously described.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

Other than in the operating examples, or where otherwise indicated, all numbers expressing quantities of ingredients or reaction conditions used herein are to be understood as modified in all instances by the term "about".

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

The terminology used herein is for the purpose of describing particular examples of apparatus for controlling reaction mixtures temperatures is not intended to be limiting. Unless defined otherwise, all technical and scientific terms used herein have the same meaning as commonly understood by one having ordinary skill in the art. The recitation of a numerical range using endpoints includes all numbers subsumed within that range (e.g., 1 to 5 includes 1, 1.5, 2, 2.75, 3, 3.80, 4, 5, etc.).

The terms "preferred" and "preferably" may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Features of different examples may be used in conjunction or interchangeably, and the examples described are for the purpose of example only.

Although the invention has been described with reference to specific examples, it will be appreciated by those skilled in the art that the invention may be embodied in many other forms. In particular features of any one of the various described examples may be provided in any combination in any of the other described examples.

The claims defining the invention are as follows:

1. Apparatus for controlling the temperature of a reaction mixture held within a reaction container supported in a rotatable carousel, the apparatus comprising:

a) a radiation source for exposing the reaction container to radiation thereby heating the reaction mixture, wherein the radiation source is circular, is subjacent to the reaction container, extends around the entire perimeter of the rotatable carousel, and is adapted to selectively generate a predetermined heating zone;

b) a temperature sensor comprising an infra-red sensor for sensing a temperature indicative of a reaction mixture temperature;

c) a controller for controlling the radiation source in accordance with the reaction mixture temperature to thereby selectively heat the reaction mixture;

d) a coolant supply port comprising a plurality of apertures disposed adjacent the radiation source and adapted to selectively generate a predetermined cooling zone; and e) a base plate comprising said coolant supply port and a reflector plate, wherein the reflector plate is parabolic in cross section, the radiation source is located within a trough of the reflector plate and the heat generated by the radiation source is primarily directed towards the reaction container, wherein said predetermined heating zone and predetermined cooling zone are generated substantially adjacent to the radiation source and the coolant supply port respectively, such that the temperature of the reaction mixture is controllable by selective exposure of the reaction container to the heating zone and/or the cooling zone.

2. Apparatus according to claim 1, wherein the apparatus comprises a heat source for heating a chamber comprising the reaction container.

3. Apparatus according to claim 2, wherein the controller is for:

a) increasing the temperature of the reaction mixture at least in part using the radiation source; and, b) maintaining the temperature of the reaction mixture at least in part using the heat source.

4. Apparatus according to claim 1, wherein the apparatus comprises a cooling mechanism for cooling the reaction mixture.

5. Apparatus according to claim 4, wherein the cooling mechanism is for cooling the reaction mixture from an elevated temperature.

6. Apparatus according to claim 4, wherein the cooling mechanism supplies ambient air to a chamber comprising the reaction container.

7. Apparatus according to claim 4, wherein the cooling mechanism supplies chilled fluid to a chamber comprising the reaction container.

8. Apparatus according to claim 1, wherein the temperature sensor comprises an optical sensor for sensing a colour of a temperature dependent indicator in the reaction mixture.

9. Apparatus according to claim 1, wherein the temperature sensor senses the temperature of the reaction mixture.

10. Apparatus according to claim 1, wherein the temperature sensor senses a reaction container temperature and wherein the controller is for determining the reaction mixture temperature using the reaction container temperature.

11. Apparatus according to claim 1, wherein the temperature sensor senses a chamber temperature and wherein the controller is for determining the reaction mixture temperature using the chamber temperature.

12. Apparatus according to claim 1, wherein the radiation source generates infra-red radiation.

13. Apparatus according to claim 1, wherein the radiation source generates optical radiation.

14. Apparatus according to claim 1, wherein the apparatus includes a chamber for receiving the reaction containers in use.

15. Apparatus according to claim 1, wherein the apparatus includes a mounting for receiving a number of reaction containers, the radiation source and mounting being arranged to allow heating of at least one of the number of reaction containers.

16. Apparatus according to claim 15, wherein the apparatus includes a drive for moving the mounting relative to the radiation source.

17. Apparatus according to claim 16, wherein the controller is for controlling the drive to thereby selectively heat reaction mixture in respective ones of the number of reaction containers.

18. Apparatus according to claim 1, wherein the radiation source exposes a heating zone to radiation and wherein the controller controls heating of the reaction mixture by selectively exposing the reaction container to the heating zone.

19. Apparatus according to claim 1, wherein the controller comprises a processing system.

20. Apparatus according to claim 1, wherein the controller is for:

a) increasing the reaction mixture temperature to a first temperature value to denature polynucleotides in the reaction mixture;

b) decreasing the reaction mixture temperature to a second temperature value to anneal polynucleotides in the reaction mixture; and, c) increasing the reaction mixture temperature to a third temperature value to hybridize the denatured polynucleotides.

21. Apparatus according to claim 1, wherein the controller is for:

a) determining the reaction mixture temperature using signals received from the temperature sensor; and, b) controlling the radiation source based on the reaction mixture temperature, allowing the reaction mixture temperature to be controlled.

22. Apparatus according to claim 1, wherein the controller is for:

a) controlling the radiation source to increase the reaction mixture temperature to a first temperature value;

b) controlling a heat source to maintain the reaction mixture temperature at the first temperature value;

c) controlling a cooling mechanism to thereby decrease and maintain the reaction mixture temperature at a second temperature; and, d) controlling the radiation source to thereby increase the reaction mixture temperature to a third temperature value; and, e) controlling the heat source to maintain the reaction mixture temperature at the third temperature value.

23. Apparatus according to claim 1, wherein the reaction container is at least partially transmissive to the radiation.

24. Apparatus according to claim 23, wherein the radiation has a wavelength selected in accordance with at least one of reaction container properties and reaction mixture properties.

25. Apparatus according to claim 1, wherein a plurality of reaction containers are provided in an array.

26. Apparatus according to claim 1, wherein the temperature of the reaction mixture is controllable by selective exposure of the reaction container to the heating zone or the cooling zone according to a predetermined thermal profile.

27. Apparatus according to claim 26 wherein the predetermined thermal profile is adapted for nucleic acid amplification.

28. Apparatus according to claim 1, wherein the heating zone and cooling zone are substantially coincident.

29. The apparatus according to claim 1, wherein the coolant supply port comprises a plurality of circumferentially spaced apertures.

30. The apparatus according to claim 1, wherein the coolant supply port comprises a plurality of circumferentially spaced apertures that are disposed adjacent the reflector plate.

31. A method for controlling the temperature of a reaction mixture held within a reaction container supported in a rotatable carousel, the method comprising:

i) providing a radiation source for exposing the reaction container to radiation, wherein the radiation source is circular, is subjacent to the reaction container, extends around the entire perimeter of the rotatable carousel, and is adapted to selectively generate a predetermined heating zone;

ii) providing a temperature sensor comprising an infra-red sensor for sensing a temperature indicative of a reaction mixture temperature;

iii) providing a controller for controlling the radiation source in accordance with the reaction mixture temperature to thereby selectively heat the reaction mixture;

iv) providing a base plate comprising a reflector plate and a coolant supply port comprising a plurality of apertures disposed adjacent the radiation source and adapted to selectively generate a predetermined cooling zone, wherein the reflector plate is parabolic in cross section, the radiation source is located within a trough of the reflector plate and the heat generated by the radiation source is primarily directed towards the reaction container;

wherein said predetermined heating zone and predetermined cooling zone are generated substantially adjacent to the radiation source and the coolant supply port respectively, and v) controlling the temperature of the reaction mixture by selective exposure of the reaction container to the heating zone and/or the cooling zone.

32. The method of controlling the temperature of a reaction mixture held within a reaction container according to claim 31, further comprising, in said controller, a) determining a reaction mixture temperature using signals received from the temperature sensor; and, b) controlling the radiation source based on the reaction mixture temperature.

* * * * *